US 11,156,676 B2

(12) United States Patent
Honkura et al.

(10) Patent No.: US 11,156,676 B2
(45) Date of Patent: Oct. 26, 2021

(54) GSR SENSOR ELEMENT

(71) Applicant: ASAHI INTECC CO., LTD., Aichi (JP)

(72) Inventors: Yoshinobu Honkura, Chita-gun (JP); Eiki Kikuchi, Tokai (JP); Kazue Kudo, Nagoya (JP); Junichi Tanabe, Nagoya (JP); Shinpei Honkura, Chita-gun (JP)

(73) Assignee: ASAHI INTECC CO., LTD., Seto (JP)

( * ) Notice: Subject to any disclaimer, the term of this patent is extended or adjusted under 35 U.S.C. 154(b) by 187 days.

(21) Appl. No.: 16/441,040

(22) Filed: Jun. 14, 2019

(65) Prior Publication Data

US 2019/0302195 A1    Oct. 3, 2019

Related U.S. Application Data

(63) Continuation of application No. PCT/JP2018/018555, filed on May 14, 2018.

(30) Foreign Application Priority Data

Jun. 5, 2017    (JP) ............................ JP2017-110509

(51) Int. Cl.
*G01R 33/06* (2006.01)
*A61B 5/0533* (2021.01)
(Continued)

(52) U.S. Cl.
CPC .......... *G01R 33/066* (2013.01); *A61B 5/0533* (2013.01); *G01R 33/02* (2013.01); *H01L 29/82* (2013.01)

(58) Field of Classification Search
CPC .... G01R 33/066; G01R 33/02; G01R 33/063; H01L 29/82; A61B 5/0533; A61B 2562/0223; A61B 5/062; A61B 5/063
See application file for complete search history.

(56) References Cited

U.S. PATENT DOCUMENTS

2010/0231222 A1    9/2010  Bazinet
2011/0089512 A1*   4/2011  Honkura ............... G01R 33/18
                                              257/427

(Continued)

FOREIGN PATENT DOCUMENTS

JP    2001-52947 A     2/2001
JP    2005-315812 A    11/2005

(Continued)

OTHER PUBLICATIONS

Singapore Office Action dated Mar. 3, 2020 in Singapore Application No. 11201905543Q.

(Continued)

*Primary Examiner* — Ryan W Sherwin
(74) *Attorney, Agent, or Firm* — Xsensus LLP

(57) ABSTRACT

In a GSR sensor element, tm and ti of rising pulse detection are close, and the induced voltage is significantly high at tm. Thus, a variation due to the magnetic field cannot be ignored. To remove an induced voltage from an output voltage and achieve a GSR sensor with a rising pulse detection system. On the basis of the knowledge that the polarity of an induced voltage becomes opposite relative to a direction of the current flowing in a magnetic wire, if one coil includes therein two magnetic wires in which currents of opposite polarities flow, an induced current is cancelled, allowing for the detection of a voltage in proportion to a magnetic field.

8 Claims, 10 Drawing Sheets

(51) Int. Cl.
*G01R 33/02* (2006.01)
*H01L 29/82* (2006.01)

(56) References Cited

U.S. PATENT DOCUMENTS

| | | |
|---|---|---|
| 2013/0181705 A1 | 7/2013 | Honkura et al. |
| 2015/0338474 A1 | 11/2015 | Mohan et al. |
| 2016/0116551 A1* | 4/2016 | Ra .................. G01R 33/063 |
| | | 324/258 |
| 2016/0238673 A1 | 8/2016 | Honkura |
| 2017/0074950 A1 | 3/2017 | Li et al. |

FOREIGN PATENT DOCUMENTS

| | | |
|---|---|---|
| JP | 2006-300906 A | 11/2006 |
| JP | 2008-275578 A | 11/2008 |
| JP | 5747294 B1 | 7/2015 |
| JP | 5839527 B1 | 1/2016 |
| JP | 2016-151413 A | 8/2016 |
| JP | 2017-70709 A | 4/2017 |
| WO | 2009/044820 A1 | 4/2009 |
| WO | 2013/047367 A1 | 4/2013 |
| WO | 2013/047637 A1 | 4/2013 |

OTHER PUBLICATIONS

International Search Report and Written Opinion dated Jul. 31, 2018 for PCT/JP2018/018555 filed on May 14, 2018, 8 pages including English Translation of the International Search Report.
Indonesian Office Action dated Jul. 9, 2021, in corresponding Indonesian Patent Application No. P00201904884.

* cited by examiner

GSR SENSOR ELEMENT

CROSS-REFERENCE TO RELATED APPLICATIONS

This application is a continuation of International Patent Application No. PCT/JP2018/018555, filed on May 14, 2018, which claims the benefit of Japanese Patent Application No. 2017-110509, filed on Jun. 5, 2017, the entire contents of each are incorporated herein by reference.

FIELD

The present invention relates to a technology of improving sensitivity and reducing power consumption in a GSR sensor element having only one magnetic wire in one coil by providing, in one coil, a pair of magnetic wires in which current directions are opposite to each other.

BACKGROUND

Treatment using a catheter is used widely. However, it has caused problems of X-ray exposure, excessive use of a contrast agent, and exposure to differences in doctors' degree of skill. To solve such problems, the establishment of remote-control catheter treatment using values of a position or a direction of a tip of a catheter measured by a magnetic sensor embedded in the catheter has been desired.

However, the GSR described in Patent Literature 1 has not been sufficient in linearity, sensitivity, compactness in size, and power consumption.

That is, if a rising pulse detection is adopted, the linearity is not preferable, and if a falling pulse detection is adopted, the sensitivity and the power consumption are not preferable. Thus, it has been difficult to downsize the ASIC of the element.

Moreover, if the element is downsized, the sensitivity is deteriorated. Thus, it has been difficult to significantly downsize the element. The solution to such problems has been sought.

The present invention improves sensitivity and power consumption while securing excellent linearity, even if rising pulse detection is adopted. Moreover, the present invention significantly improves sensitivity, which enables the downsizing of the element. The reduction of power consumption significantly reduces the capacitance of the capacitor in the ASIC, which also downsizes the ASIC.

CITATION LIST

Patent Literature

Patent Literature 1: Japanese Patent No. 5839527

SUMMARY

Technical Problem

It is conventionally known that in a GSR sensor, if two magnetic wires are arranged in one coil, the sensitivity doubles, and if rising pulse detection is adopted, the pulse power consumption can be reduced to $\frac{1}{10}$ from 0.4 mW to 0.04 mW.

Here, the GSR sensor is a super-high-sensitivity micro magnetic sensor based on the GHz spin rotation effect.

However, the output voltage of the GSR sensor element includes two kinds of voltages: a voltage induced by a pulse current (hereinafter, referred to as an induced voltage) and a voltage output in proportion to the intensity of an external magnetic field (hereinafter, referred to as a magnetic field voltage). Moreover, it is troublesome that the magnetic field changes a resistance of a magnetic wire, and thus makes an influence on the variation of a wire voltage and the induced voltage.

In the falling pulse detection, the peak time tm of a magnetic field voltage is separate from the peak time ti of an induced voltage, and the induced voltage is sufficiently attenuated at time tin (FIG. 7).

Meanwhile, in the rising pulse detection, tm is close to ti, and the induced voltage is significantly high at the time tm. Thus, the variation due to the magnetic field cannot be ignored (FIG. 8). The present invention aims at removing the induced voltage from the output voltage of the GSR element and achieving a GSR sensor with a rising pulse detection system.

Solution to Problem

As a result of intensive study of the above-described technical problems, the inventors found that the polarity of an induced voltage becomes opposite relative to the direction of the current flowing in a magnetic wire. Then, they arrived at the technical idea of the present invention that if one coil includes therein two magnetic wires in which currents of opposite polarities flow, an induced voltage is cancelled, allowing for the detection of only a voltage in proportion to a magnetic field.

Regarding the typical size of a coil in a GSR sensor element with one magnetic wire, the groove width is 20 μm, and the coil width is 40 μm. In the GSR sensor element with two magnetic wires, the groove width is 40 μm, in which two magnetic wires are arranged with a separation wall (or an insulating wall) in the center, and the coil width is 50 μm. The size of the GSR sensor element is almost the same for one magnetic wire and for two magnetic wires.

Three kinds of structures exist for the element.

The first structure is a type in which two magnetic wires are arranged in a groove deeper than a magnetic wire, with the lower coil having a recessed shape and the upper coil having a plane surface shape. The second structure is a type in which two magnetic wires are arranged in a shallow groove of about half of the diameter of a magnetic wire, with the lower coil having a recessed shape and the upper coil having a convex shape.

The third structure is a type in which a chevron-shaped guide is formed on a plane surface and each of the two magnetic wires is arranged in it, with the lower coil having a plane surface shape and the upper coil having a convex shape.

In any kind of structure, a separation wall is provided between the two magnetic wires.

The lower coil is arranged to deviate by a half pitch from the upper coil, and they are electrically connected on a joint surface thereof on the plane surface board to form a spiral coil. Each of two end parts of the coil is connected to two coil electrodes.

Insulation between the magnetic wire and the coil is achieved by a method of adopting a magnetic wire coated with an insulating material, a method of inserting a magnetic wire in an insulating resist embedded in a groove, or a method combining both. To secure the insulation, it is preferable to use a magnetic wire coated with an insulating material.

At the end part of the magnetic wire, a metal part of the magnetic wire is exposed from an insulating material and subject to wiring for electrical jointing to wire electrodes.

The output of the GSR sensor element using two magnetic wires maintains excellent linearity even with the rising pulse detection for only a magnetic field voltage in proportion to a magnetic field.

The output voltage of rising pulse detection is 2.5 times the output voltage of falling pulse detection. Furthermore, such a GSR sensor element has two magnetic wires, and thus it is possible to obtain output voltage that is 5 times greater. This indicates the possibility of downsizing the element because the number of windings of a coil N can be ⅕ and a coil length of the element can be ⅕.

In addition, a pulse width of a pulse current can be a sufficiently long pulse width required for rising pulse detection, from 10 ns to 1 ns or less, for example. This reduces the power consumption of a pulse current to ¹⁄₁₀ or less.

The GSR sensor ASIC includes a capacitor for storing power for pulse current transmission. The size of the capacitor occupies 50% of the ASIC. If the size of the capacitor can be reduced to ¹⁄₁₀, the size of the ASIC can be reduced to almost half.

Advantageous Effects of Invention

The GSR sensor element with two magnetic wires in one coil removes induced voltage components of the coil voltage to improve the linearity of an output voltage, which is dependent on a magnetic field, in rising pulse detection, increase sensitivity (output voltage per unit of magnetic field intensity of 1 G) fivefold, and reduce the power consumption of a pulse current to ¹⁄₁₀ or less. In this manner, it is possible to downsize the element and the ASIC under the same conditions of output voltages.

DESCRIPTION OF EMBODIMENTS

Figure 1:
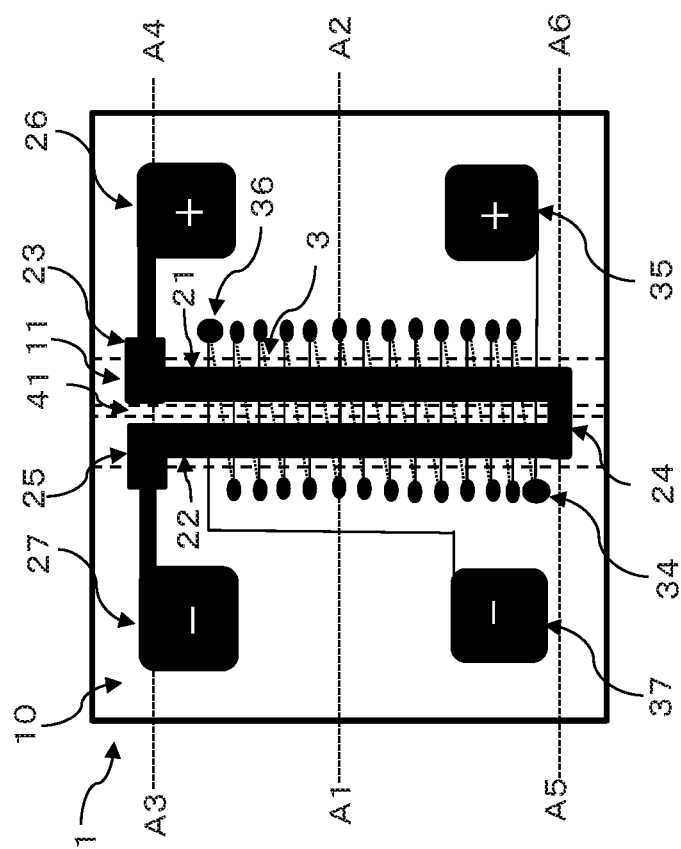
FIG. 1 is a schematic diagram illustrating a front surface of a GSR sensor element according to an embodiment and an example.

A GSR sensor element 1 of the present embodiment includes, on an electrode wiring board 10, a Co alloy magnetic wire 2 (21 and 22) coated with an insulating film, a coil 3 (31 and 32) wound around the magnetic wire 2, and four terminals (23 and 25, 34 and 36), as illustrated in FIG. 1, FIG. 2A, FIG. 2B, and FIG. 2C.

As the magnetic wire 2, there are arranged two magnetic wires 21 and 22, which are separated by an insulating wall 41, in a groove 11 on a center part of a board.

Figure 2A:
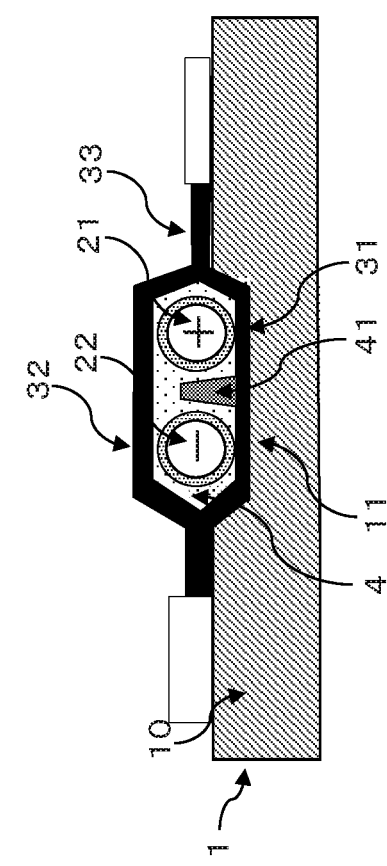
FIG. 2A is a sectional view illustrating the GSR sensor element viewed along the A1-A2 line of FIG. 1 according to the embodiment.
Figure 2B:
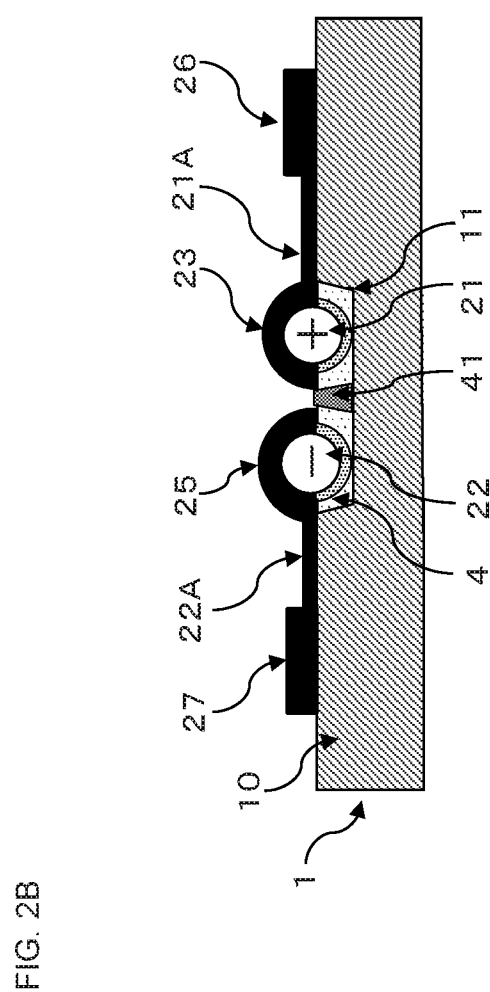
FIG. 2B is a sectional view illustrating the GSR sensor element viewed along the A3-A4 line of FIG. 1 according to the embodiment.

The upper part of the magnetic wire 21 on the wire input electrode 26(+) side, illustrated on the right side of FIG. 1, is connected to a wire input electrode 26(+) through the wire terminal 23 and a wire connection portion 21A (right part of FIG. 2B).

Figure 2C:
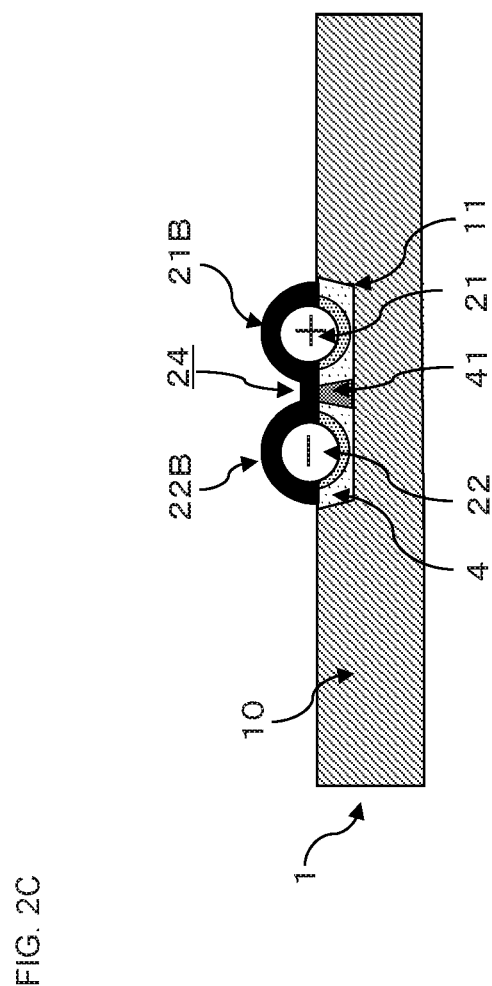
FIG. 2C is a sectional view illustrating the GSR sensor element viewed along the A5-A6 line of FIG. 1 according to the embodiment.

The lower part of the magnetic wire 21 is connected to the lower part of the magnetic wire 22 on the wire output electrode 27(−) side through a wire joint part 22B illustrated on the left side through a wire joint part 21B and a wire connection portion 24 (FIG. 2C).

The upper portion of the magnetic wire 22 is connected to a wire output electrode 27(−) through the wire terminal 25 (left part of FIG. 2B).

Next, the coil 3 includes a lower coil 31, an upper coil 32, and a joint part 33 jointing both coils.

The lower coil 31 is formed in a recessed shape in the groove 11 and on the board 10, while the upper coil 32 is formed from the upper part of a pair of magnetic wires 21 and 22 to the side through an insulating material 4 and then onto the board 10.

The end part of the lower coil 31 and the end part of the upper coil 32 form the joint part 33 on the board 10 to be connected to each other.

Note that the pair of magnetic wires 2 (21 and 22) are insulated from each other by the insulating wall 41, and the magnetic wire 2 is insulated from the coil 3 by the insulating material 4.

In this manner, a current flows downward in the magnetic wire 21 on the right side, while a current flows upward in the magnetic wire 22 on the left side, whereby in one coil, the directions of currents are opposite from each other through the insulating material, which cancels an induced voltage.

In the present embodiment, a pair of magnetic wires formed of two magnetic wires is arranged in one coil so that the current directions thereof are opposite from each other through the insulating material. However, a plurality of pairs of magnetic wires may be arranged in one coil.

Moreover, in the present embodiment, as the magnetic wire, there is used a magnetic wire coated with glass that is the insulating material. However, it is also possible to use a magnetic wire not coated with an insulating material.

In the present embodiment, the structure of the element is of the type in which two magnetic wires (21 and 22) are arranged in the shallow groove 11 of about half of the diameter of the magnetic wire 2, and the lower coil 31 has a recessed shape and the upper coil 32 has a convex shape, as illustrated in FIG. 2A.

Figure 3:
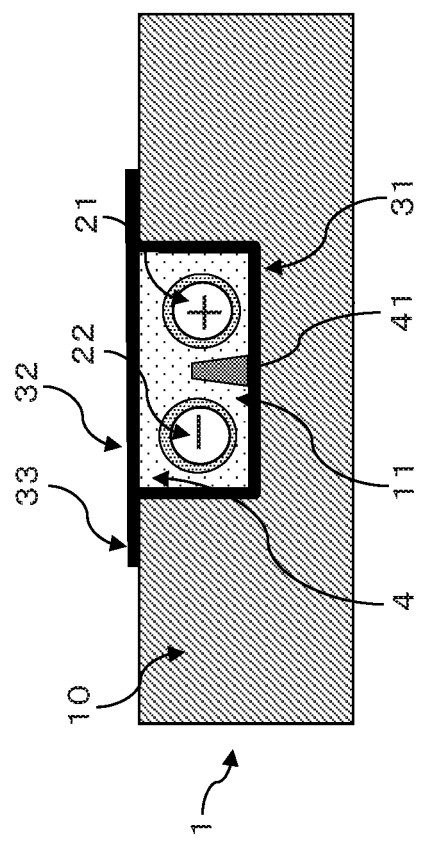
FIG. 3 is a sectional view illustrating another type (recessed shape) of the GSR sensor element according to the embodiment.
Figure 4:
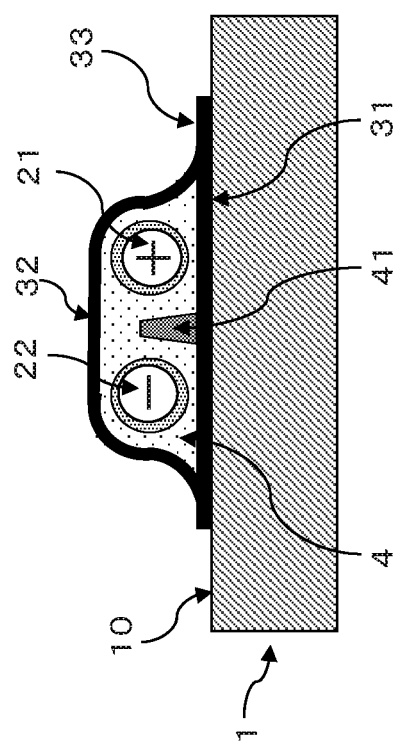
FIG. 4 is a sectional view illustrating another type (convex shape) of the GSR sensor element according to the embodiment.

As another type of structure, two magnetic wires (21 and 22) are arranged in the groove 11 deeper than the magnetic wire 2, and the lower coil 31 has a recessed shape and the upper coil 32 has a plane surface shape, as illustrated in FIG. 3. Moreover, the third type of structure is of the type in which a chevron-shaped guide is formed on a plane surface and each of the two magnetic wires (21 and 22) is arranged in it, and the lower coil 31 has a plane surface shape, and the upper coil 32 has a convex shape, as illustrated in FIG. 4.

In any kind of structure, the insulating wall 41 is provided between the two magnetic wires (21 and 22). The joint part 33 connecting the end part of the lower coil 31 and the end part of the upper coil 32 is provided to form the coil 3.

The following will describe a method of manufacturing the GSR sensor element.

For the electrode wiring board 10, there is used a Si substrate coated with SiN. For the magnetic wire 2, there is used an amorphous wire having a diameter of 1 to 20 μm and a length of 0.07 to 1.0 mm coated with a glass insulating film.

First, in the element 1 having a width of 0.25 mm, the groove 11 with a width of 20 to 60 μm and a depth of 2 to 20 μm is formed in the center part thereof.

Next, electrode wiring is performed in the lower coil 31 and on the board surface along the groove 11. Then, the insulating wall 41 is formed in the center part of the groove 11 to have a two-groove form, and each one of the two magnetic wires 21 and 22 is arranged therein. Thereafter, an insulating resist is applied onto the entire surface of the board. The insulating resist is applied thinly in the upper part of the two magnetic wires (21 and 22). At that part, the upper coil 32 is formed by photolithographic technology.

The joint part 33 is formed to diagonally join the end parts of the lower coil 31 and the upper coil 32 on the board surface, so as to form the coil 3 with a coil pitch of 2 to 10 μm. A coil terminal 34 is connected to a coil output electrode 35(+), and a coil terminal 36 is connected to a coil ground electrode 37(−).

At the four ends of the two magnetic wires, the glass as an insulating film is removed. The wire terminal 23 and the wire connection portion 21A are formed at one of the two ends by metal vapor deposition to enable electrical connection to a wire input electrode 26(+), while the wire terminal 25 and a wire connection portion 22A are formed at the other end by metal vapor deposition to enable electrical connection to a wire output electrode 27(−).

Then, the other two end parts are subjected to metal vapor deposition (21B and 22B), and a connection portion 23 connecting the two end parts is formed by metal vapor deposition.

In this manner, the wiring for the power supply of a pulse current is performed from the wire input electrode 26(+) to the wire output electrode 27(−).

In the present embodiment, the output voltage exhibits sine wave output characteristics relative to a magnetic field H, and the linearity is 0.3% or lower in a measurement range of ±3 to 90 G, which is excellent.

The sensitivity is 50 to 2000 mV/G and is about five times higher than that of the GSR sensor element having the same length of magnetic wire.

The pulse power consumption is 0.3 mW (0.15 mA).

Example

Figure 5:
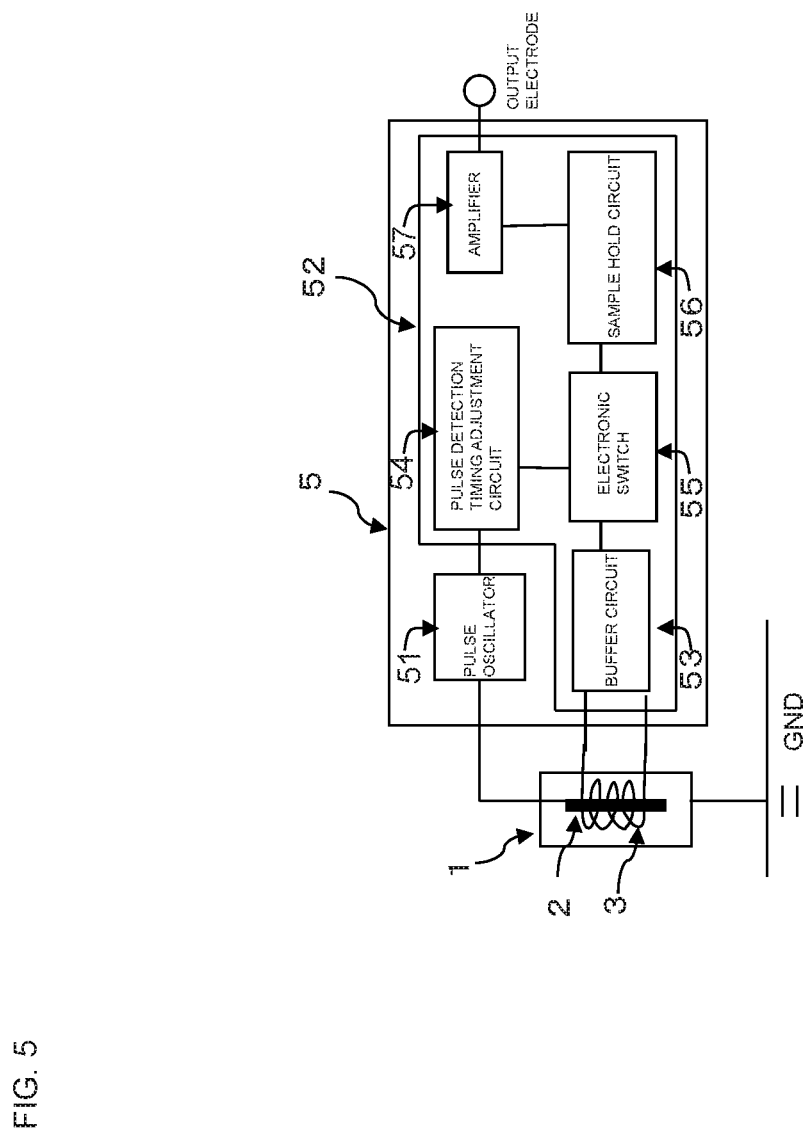
FIG. 5 is a block circuit diagram illustrating an electronic circuit of the GSR sensor according to the example.
Figure 6:
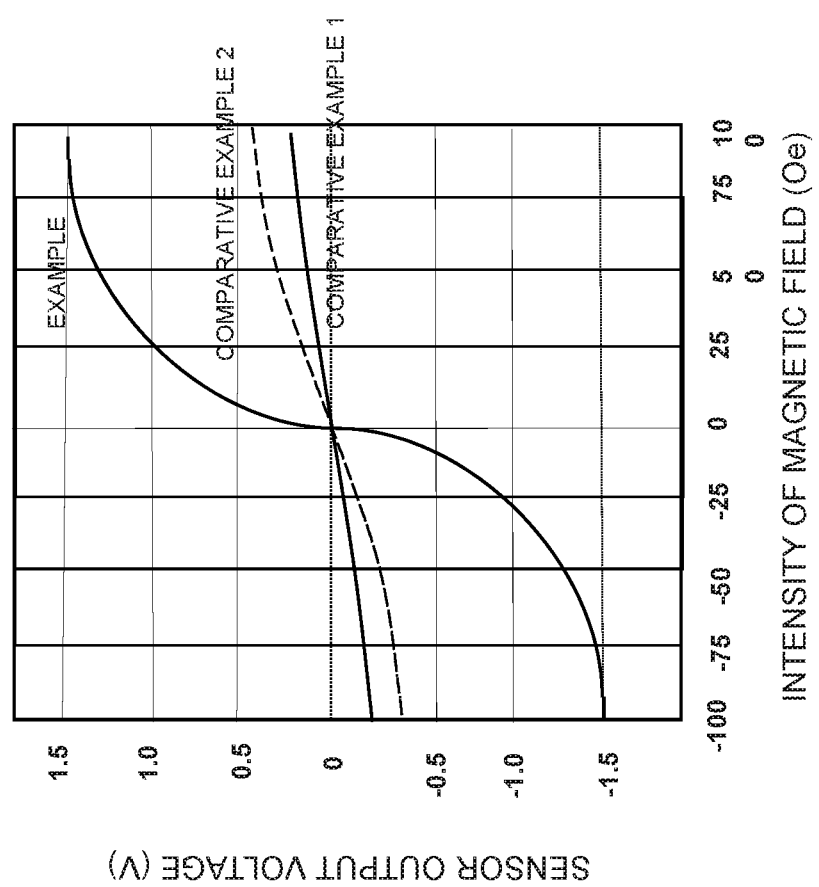
FIG. 6 is a characteristic diagram illustrating the relation between an external magnetic field and an output voltage of the magnetic sensor in the GSR sensor according to the example and comparative examples.
Figure 7:
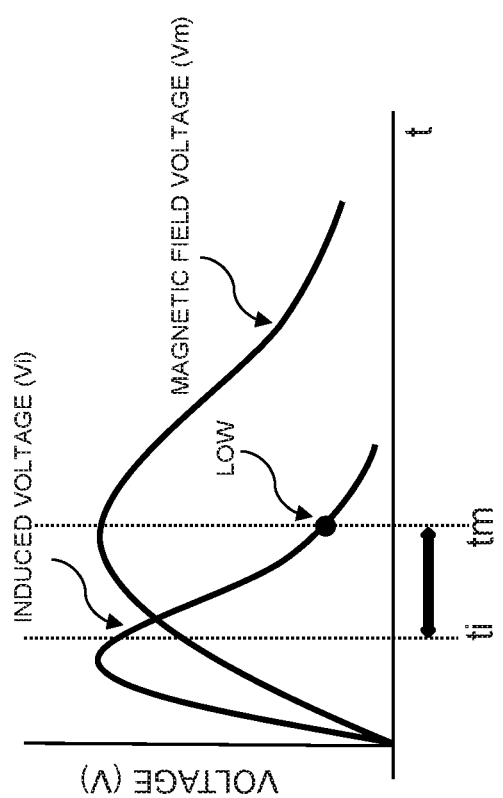
FIG. 7 is a progress diagram of the temporal change of a magnetic field voltage and an induced voltage in falling pulse detection.
Figure 8:
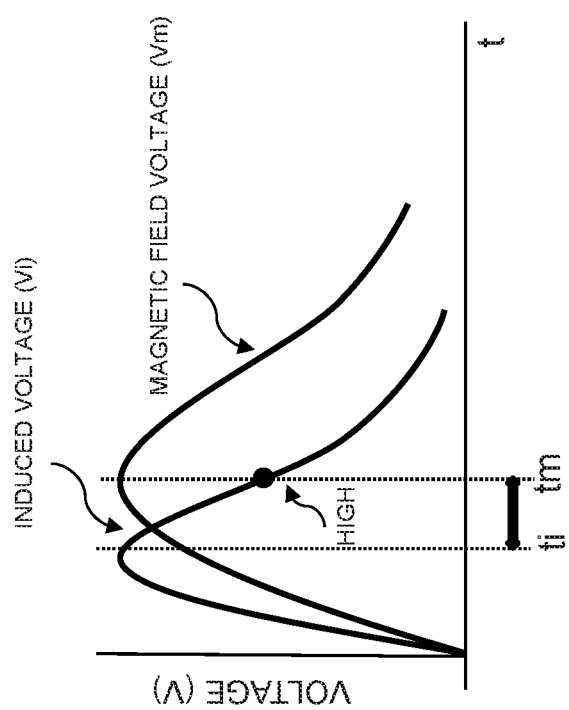
FIG. 8 is a progress diagram of the temporal change of a magnetic field voltage and an induced voltage in rising pulse detection.

The following will describe the GSR sensor element according to an example of the present invention with reference to FIG. 1, FIG. 5, and FIG. 6.

The board 10 is formed of an Si substrate insulated and coated with SiN. The size of the board 10 is 0.2 mm in length, 0.2 mm in width, and 0.2 mm in height. The magnetic wire 2 is an amorphous wire of a CoFeSiB-based alloy having a diameter of 10 μm and a length of 0.20 mm coated with glass.

The width of the groove 11 of the board 10 is 40 μm, and the depth thereof is 6 μm. The size of the insulating wall 41 formed by an insulating resist in the groove 11 has a width of 2 μm and a height of 6 μm.

The coil 3 has a width of 50 μm, a height of 14 μm, and an average internal diameter (diameter of a circle equivalent to a sectional area in a coil formed by a height and a width) of 26 μm. The coil pitch is 5 μm, and the number of windings of the coil is 28.

Next, the characteristics of the GSR sensor element 1 were evaluated using an electronic circuit for an MI sensor illustrated in FIG. 5.

The electronic circuit 5 includes a pulse oscillator 51, the GSR sensor element 1, and a signal processing circuit 52 including a buffer circuit 53. The signal is a pulse signal with an intensity of 100 mA equivalent to 1 GHz, and inputs a pulse current with a rising time of 0.5 nsec, a pulse width of 1 nsec, and a falling time of 0.5 nsec.

The pulse signal is input to the amorphous wire 2, and during the pulse applying operation, a voltage in proportion to the external magnetic field occurs in the magnetic coil 3, which is subject to rising pulse detection.

The signal processing circuit 52 inputs the voltage occurred in the coil 3 to the buffer circuit 53, and the output from the buffer circuit 53 is input to a sample hold circuit 56 through an electronic switch 55. The timing of opening and closing of the electronic switch 55 is adjusted by a pulse detection timing adjustment circuit 54 to allow detection at a timing adequate for rising pulse signals, and the voltage at the time is sampled and held. Thereafter, the voltage is amplified to a given voltage by an amplifier 57.

FIG. 6 illustrates sensor output from the electronic circuit. In FIG. 6, the horizontal axis shows the intensity of an external magnetic field, and the vertical axis shows a sensor output voltage.

The sensor output exhibits sine wave output characteristics, and shows the linearity in a range of ±90 G by arcsin conversion. The nonlinearity is 0.3%. The sensitivity is 210 mV/G.

An MI element used for the product on the market AMI306 (length: 0.6 mm, width: 0.3 mm) as Comparative Example 1, and a GSR sensor element for vehicles (length: 0.15 mm, width: 0.20 mm) as Comparative Example 2 were subjected to measurement evaluation using the same electronic circuit. The results are illustrated by Comparative Examples 1 and 2 in FIG. 6.

Regarding the sensor output voltage at the magnetic field intensity of 90 Oe, the GSR sensor of the present invention obtains an excellent sensitivity of 1.5V relative to 0.1V in the MI sensor of Comparative Example 1 and 0.3V in the GSR sensor of Comparative Example 2.

INDUSTRIAL APPLICABILITY

As described above, the GSR sensor element of the present invention is considerably compact in size and achieves high sensitivity. In this manner, the GSR sensor formed by the element achieves significantly high sensitivity, compactness in size, and low power consumption, and thus it can be embedded in catheters. Moreover, it can also be adapted to wider fields such as smartphones.

REFERENCE SIGNS LIST

1 GSR sensor element plate
10 board 11 groove on a substrate
2 magnetic wire
21 one of a pair of magnetic wires
22 the other of a pair of magnetic wires
21A connection portion between wire terminal and wire input electrode(+)
22A connection portion between wire terminal and wire output electrode(−)
21B wire joint part
22B wire joint part
23 terminal of magnetic wire
24 connection portion between wires
25 terminal of magnetic wire
26 wire input electrode(+)
27 wire output electrode(−)
3 coil
31 lower coil
32 upper coil
33 joint part
4 insulating material
41 insulating wall
5 electronic circuit
51 pulse oscillator
52 signal processing circuit
53 buffer circuit
54 pulse detection timing adjustment circuit
55 electronic switch
56 sample hold circuit
57 amplifier

The invention claimed is:

1. A sensor, comprising:
an electrode wiring board;
a pair of magnetic wires made of a magnetosensitive body respectively, the pair of magnetic wired being formed on the electrode wiring board and arranged so that current directions thereof are opposite from each other through an insulating material;
a coil including a coil lower part, a coil upper part, and a joint part connecting the coil lower part and the coil upper part; and
four terminals formed on end parts of the coil and the pair of magnetic wires respectively for connecting to an external integrated circuit, wherein
the coil is wound around both of the pair of magnetic wires, such that each wind of the coil covers both of the pair of magnetic wires,
the pair of magnetic wires are separated by an insulating wall in the coil, the insulating wall insulating the pair of magnetic wires from each other, and
the insulating wall and both of the pair of magnetic wires are wound together by the coil.

2. The sensor according to claim 1, wherein each of the pair of magnetic wires includes a plurality of pairs of magnetic wires.

3. The sensor according to claim 1, wherein an outer periphery of each of the pair of magnetic wires is coated with the insulating material.

4. The sensor according to claim 1, wherein
the coil lower part has a recessed shape,
the coil upper part has a convex shape,
the pair of magnetic wires are embedded in a groove on the electrode wiring board coated with the insulating material and are subjected to wiring at the coil lower part and fixed by insulating resin having an adhesion function and a resist function,
an upper part of the pair of magnetic wires is covered by surface tension of the insulating resin and subjected to wiring at the coil upper part, and
the joint part electrically joints an end part of the coil lower part and an end part of the coil upper part to form the coil.

5. The sensor according to claim 1, wherein
the coil lower part has a recessed shape,
the coil upper part has a plane shape,
the pair of magnetic wires are inserted in a groove on the board having the insulating material embedded and are subjected to wiring at the coil lower part,
an upper surface of the groove is subjected to wiring at the coil upper part, and
the joint part electrically joints an end part of the coil lower part and an end part of the coil upper part to form the coil.

6. The sensor according to claim 1, wherein
the coil lower part has a plane shape,
the coil upper part has a convex shape,
the pair of magnetic wires are fixed by insulating resin on an upper surface of wiring at the coil lower part on a flat surface of the board,
a side part and an upper part of the pair of magnetic wires are covered by the insulating resin and are subjected to wiring at the coil upper part, and
the joint part electrically joints an end part of the coil lower part and an end part of the coil upper part to form the coil.

7. The sensor according to claim 1, wherein the coil upper part is manufactured by a photolithography method.

8. The sensor according to claim 1, wherein the sensor is a GHz-Spin-Rotation (GSR) sensor.

* * * * *